United States Patent [19]

Persello

[11] Patent Number: 5,074,917
[45] Date of Patent: Dec. 24, 1991

[54] NOVEL OXIDE/DYE PIGMENTARY COLORANTS

[75] Inventor: Jacques Persello, Saint Andre de Corcy, France

[73] Assignee: Rhone-Poulenc Chimie, Courbevoie, France

[21] Appl. No.: 330,353

[22] Filed: Mar. 29, 1989

Related U.S. Application Data

[63] Continuation of Ser. No. 106,806, Oct. 13, 1987, abandoned.

[30] Foreign Application Priority Data

Oct. 10, 1986 [FR] France ................................ 86 14103

[51] Int. Cl.$^5$ ........................... C09C 1/28; C09C 1/36; C09C 3/00
[52] U.S. Cl. ..................................... 106/436; 106/402; 106/447; 106/450; 106/482; 106/491; 106/499
[58] Field of Search ............... 106/402, 436, 447, 450, 106/491, 482, 499, 401

[56] References Cited

U.S. PATENT DOCUMENTS

| 3,477,866 | 11/1969 | Remer | 106/402 |
| 3,716,388 | 2/1973 | Lopez et al. | 106/402 |
| 4,167,422 | 9/1979 | Bellanca et al. | 106/402 |
| 4,769,079 | 9/1988 | Clark et al. | 106/402 |

FOREIGN PATENT DOCUMENTS 772800 4/1957 United Kingdom .
2117783 10/1983 United Kingdom .

Primary Examiner—Paul Lieberman
Assistant Examiner—Christine A. Skane
Attorney, Agent, or Firm—Burns, Doane, Swecker & Mathis

[57] ABSTRACT

Novel Pigmentary colorants, well adapted for the production of electrostatic developer powders and dentifrices, are comprised of coprecipitated/crystallized mineral oxide particulates and at least one dye. The at least one dye is at least partly physically confined within a matrix of the mineral oxide.

24 Claims, No Drawings

NOVEL OXIDE/DYE PIGMENTARY COLORANTS

This application is a continuation of application Ser. No. 106,806, filed Oct. 13, 1987 abandoned.

CROSS-REFERENCE TO COMPANION APPLICATION

Copending application, Ser. No. 07/530,442, is a continuation of 07/106,778, now abandoned, filed concurrently herewith and assigned to the assignee hereof.

BACKGROUND OF THE INVENTION

1. Field of the Invention

The present invention relates to colored pigments based on a mineral oxide of the silica, alumina or titanium or zirconium oxide-type and to processes for the production thereof.

2. Description of the Prior Art

It is well known to this art, for numerous applications, to add mineral charges to a wide variety of different materials for purposes of imparting any given number of particular properties thereto. Among the most widely encountered such properties are optical, mechanical and rheological properties.

For certain applications, it is necessary to incorporate charges combined with a pigment or dye. Generally, these charge/pigment compositions are produced by physically admixing the mineral charge with the dye or pigment. However, such process suffers from a certain number of disadvantages.

A first disadvantage is that it is difficult for a given mineral charge to contain all of the desired coloration.

Another problem is linked to the compatibility of the dye with the material intended to be provided with the pigmentation. Therefore, for a given material, as a function of said compatibility, it will only be possible to use a limited number of dyes or pigments. It is also necessary to take account of the dispersibility of the dye in the same material.

Moreover, the resulting colored compositions can display a low resistance to chemical and photochemical deterioration, as well as to abrasion.

SUMMARY OF THE INVENTION

Accordingly, a major object of the present invention is the provision of improved colorants for a given mineral charge which display the complete desired range of colors, which are compatible with a great number of materials and which also exhibit improved mechanical and chemical resistance.

Briefly, the colored pigments according to this invention feature a mineral oxide and at least one dye, the dye or dyes being at least partially incorporated within the mineral oxide itself. By the term "oxide", as utilized herein, are intended not only the oxides, per se, but also the various hydrates thereof, e.g., the hydrated oxides of the formula $MO_x \cdot (H_2O)_y$.

In a preferred embodiment of the invention, the aforementioned mineral oxide is selected from among silica, titanium dioxide, alumina, zirconium oxide and the various hydrates thereof.

The present invention also features a process for the preparation of the colored pigments as described above, comprising the stages of forming a reaction medium constituting a precursor of the mineral oxide and at least one dye, the oxide and the dye being coprecipitated or crystallized and the pigment thus formed, and separating the liquid phase from the reaction medium.

DETAILED DESCRIPTION OF THE PREFERRED EMBODIMENTS OF THE INVENTION

More particularly according to the present invention, the essentially novel characteristic of the colored pigments hereof is based on their structure, which is linked to the very nature of the process for the preparation of the pigments. According to this structure, the dye or dyes are partly or wholly incorporated within the very mass of the mineral oxide. In other words, they are at least partly contained within the matrix constituting the oxide.

As a result of this structural characteristic, the subject pigments present certain advantages. First, the dyes are able to totally mask the color of the mineral oxide, such that it is possible to obtain pigments throughout the color range. Furthermore, as the dyes are at least partly incorporated within the oxide mass, the problem of the compatibility between the dyes and the materials to be treated is resolved. Finally, for the same reason as hereinbefore, as the dye is at least partly protected by an oxide layer, the pigment will be more resistant to the chemical action of solvents during washing processes.

As a result of their abrasion resistance, the pigments according to the invention are able to resist shear forces generated during the working thereof, e.g., during kneading, extrusion or stirring operations.

The various constituents of the pigments according to the invention will now be described.

These pigments primarily comprise a mineral oxide. It is possible to use any oxide which can be used as a charge and which can be produced by precipitation or crystallization. Particularly representative are silica, titanium dioxide, alumina and zirconium oxide Any type of dye can be used. Obviously, the dyes can be used singly or in combination. The selection thereof is based on criteria well known to this art and as a function of the desired result. Exemplary dyes are as follows. They are arranged in groups. For a given group, each paragraph reflects the name of the dye and its number in the Colour Index (C.I.).

Obviously, one or more dyes can be used according to the invention. It will thus be appreciated that when reference is made hereinafter to a single dye, it can also apply to several dyes.

| DYES | |
|---|---|
| C. I. No. | C. I. generic name |
| Anthraquinone | |
| 65 300 | Pigment Red 177 |
| — | Pigment Yellow 147 |
| 60 010 | Pigment Violet 31 |
| 60 505 | Solvent Red 111 |
| 61 110 | Solvent Blue 68 |
| 58 840 | Solvent Yellow 163 |
| — | Solvent Blue 132 |
| — | Solvent Blue 122 |
| — | Acid Blue 183 |
| — | Solvent Blue 225 |
| Dioxazine | |
| — | Pigment Violet 37 |
| Flaranthrone | |
| 70 600 | Pigment Yellow 24 |
| Indanthrone | |
| 69 800 | Pigment Blue 60 |

-continued

| DYES | | |
|---|---|---|
| | | C. I. generic name |
| Quinacridone | | |
| 73 900 | | Pigment Violet 19 |
| | | Pigment Red 202 |
| | | Pigment Red 207 |
| Azo condensation | | |
| | | Pigment Yellow 128 |
| | | Pigment Yellow 93 |
| | | Pigment Yellow 94 |
| | | Pigment Yellow 95 |
| | | Pigment Orange 31 |
| | | Pigment Brown 23 |
| | | Pigment Red 166 |
| | | Pigment Red 220 |
| | | Pigment Red 144 |
| | | Pigment Red 248 |
| | | Pigment Red 221 |
| Copper-phthalocyanine alpha | | |
| 74 160 | | Pigment Blue 15 |
| 74 160 | | Pigment Blue 15:1 |
| 74 160 | | Pigment Blue 15:2 |
| Copper-phthalocyanine beta | | |
| 74 160 | | Pigment Blue 15:3 |
| 74 160 | | Pigment Blue 15:4 |
| Copper-phthalocyanine halogenated | | |
| 74 260 | | Pigment Green 7 |
| 74 265 | | Pigment Green 36 |
| | C.I. No. | |
| Isoindolinone | | |
| Orange 26 | — | Pigment Orange 61 |
| | — | Pigment Yellow 109 |
| | 56 280 | Pigment Yellow 110 |
| Azomethine | | |
| Copper complex | — | Pigment Yellow 129 |
| Nickel complex | — | Pigment Orange 65 |
| Perylene | | |
| | 71 217 | Pigment Red 224 |
| Arylamide | | |
| Arylamide 106 | 11 710 | Pigment Yellow 3 |
| Arylamide 6 | 11 680 | Pigment Yellow 1 |
| Arylamide | 11 741 | Pigment Yellow 74 |
| Diarylide | | |
| Diarylide anilide | 21 090 | Pigment Yellow 12 |
| Diarylide m-xylidiole | 21 100 | Pigment Yellow 13 |
| Diarylide o-toluidiole | 21 095 | Pigment Yellow 14 |
| Diarylide p-toluidiole | 21 096 | Pigment Yellow 55 |
| Diarylide 0-anisidiole | 21 105 | Pigment Yellow 17 |
| Diarylide dimethoxy chloranilide | 21 108 | Pigment Yellow |
| Diarylide pyrazolone | 21 110 | Pigment Orange 13 |
| Diarylide pyrazolone | 21 115 | Pigment Orange 34 |
| Diarylide pyrazolone | 21 120 | Pigment Red 38 |
| Azo dyes | | |
| Azo (Ca) | 13 880 | Pigment Yellow 61 |
| | 13 940 | Pigment Yellow 62:1 |
| Azo (Ba) | 15 602 | Pigment Red 46 |
| Azo 2 B (Ca) | 15 865:2 | Pigment Red 48:2 |
| Azo 2 B (Ba) | 15 865:1 | Pigment Red 48:1 |
| Azo 2 B toner (Sr) | 15 865:3 | Pigment Red 48:3 |
| Azo 2 B toner (Mg) | 15 865:5 | Pigment Red 48:5 |
| Azo 2 B toner (Mn) | 15 865:4 | Pigment Red 48:4 |
| Azo 4 B toner (Ca) | 15 850:1 | Pigment Red 57:1 |
| Azo (Mn) | 15 825:4 | Pigment Red 58:4 |
| Azo | 11 765 | Pigment Yellow 49 |
| | 12 470 | Pigment Orange 22 |
| | — | Pigment Red 222 |
| Dinitralinine orange | 12 075 | Pigment Orange 5 |
| Naphthol | | |
| Naphthol red | 12 085 | Pigment Red 4 |
| Naphthol AS | 12 310 | Pigment Red 2 |
| Naphthol AS | 12 370 | Pigment Red 112 |
| Naphthol AS | 12 355 | Pigment Red 23 |
| Naphthol AS | 12 385 | Pigment Red 12 |
| Naphthol AS | 12 420 | Pigment Red 7 |
| Naphthol AS | 12 490 | Pigment Red 5 |
| Toluidine | | |
| Toluidine red | 12 120 | Pigment Red 3 |
| BON (Mn) | 15 880:2 | Pigment Red 63:2 |
| BON (Mn) | 15 860:2 | Pigment Red 52:2 |
| Lake Red C (Ba) | 15 585:1 | Pigment Red 53:1 |
| Basic dye toner | 45 160:3 | Pigment Red 81:1 |
| | 45 160:2 | Pigment Red 169 |
| | 45 535:2 | Pigment Violet 3 |
| | 42 535:3 | Pigment Violet 27 |
| | 42 595:2 | Pigment Blue 1 |
| | — | Pigment Blue 62 |
| | — | Pigment Green 45 |
| Iron complex (Na) | 10 006 | Pigment Green 8 |
| Lead sulfochromate | 77 600/ 77 603 | Pigment Yellow 34 |
| Lead chromate | 77 600 | Pigment Yellow 34 |
| Lead sulfochromate molybdate mixture | 77 605 | Pigment Red 104 |
| Metal-free monoazo dye | — | Solvent Yellow 146 |
| Chrome complexes | — | Acid Yellow 118 |
| Chrome complexes | — | Acid Orange 88 |
| Chrome complexes | — | Acid Brown 21 |
| Chrome complexes | — | Acid Red 211 |
| Chrome complexes | — | Acid Black 172 |
| Chrome complexes | 18 690 | Solvent Yellow 21 |
| Chrome complexes | — | Solvent Red 213 |
| Chrome complexes | — | Solvent Red 7 |
| Chrome complexes | — | Solvent Red 214 |
| Chrome complexes | — | Solvent Yellow 88 |
| Chrome complexes | — | Solvent Orange 59 |
| Chrome complexes | — | Solvent Red 130 |
| Cobalt complexes | — | Solvent Yellow 79 |
| Cobalt complexes | — | Solvent Yellow 25 |
| Cobalt complexes | — | Solvent Orange 11 |
| Cobalt complexes | — | Solvent Red 125 |
| Cobalt complexes | — | Solvent Violet 24 |

Also exemplary are nickel complexes and amino complexes of copper, nickel and cobalt.

The amount of dyes present in the pigments of the invention can vary over wide ranges. Generally, the weight ratio between the dye and the mineral oxide is at most equal to 10%. There obviously is no reason to prevent the use of a larger amount. However, this would be of little interest because it would appear that, as a result of the process of the invention, and in order to obtain identical colors, it is generally necessary to use ten times less dye than in the prior art processes by mixing. Thus, the weight ratio between the dye and mineral oxide generally ranges from 0.001 to 10%

Finally, in general terms, it should be noted that the use of cationic or basic dyes is preferred in the case of silica-based pigments and acid or anionic dyes in the case of alumina-based pigments.

The use of hydrosoluble dyes is also preferred, when the preparative processes are carried out in an aqueous medium. For those carried out in an alcoholic medium, the use of alcohol-soluble dyes is preferred.

The process for the preparation of the pigmentary material according to the invention will now be described in greater detail.

The basic principle of the subject process includes forming the mineral oxide in the presence of the selected dye or dyes. It is obvious that it is possible to use any known precipitation or crystallization process, particularly for the preparation of the silica, alumina, titanium oxide or zirconium oxide, to the extent that such preparation can be carried out in the presence of a dye. Thus, the processes described hereinafter are only given by way of example and one skilled in this art could naturally substitute other techniques.

In the case of a silica-based colored pigment, two methods are particularly representative:

The first method comprises forming the reaction medium by intimately contacting the dye, a silicate and an acid. In this case, two variants are possible. According to the first variant, the silica is prepared by the simultaneous addition of the acid and an aqueous silicate solution. The dye can be present in the sediment prior to the simultaneous introduction of the reagents, or can be introduced simultaneously with said reagents. In the latter case, the dye is either supplied separately, or in the form of a solution in the silicate.

According to a special embodiment of this first variant, the acid and silicate can be introduced by maintaining the pH of the reaction medium constant In general, said pH is fixed at from 8 to 9. A wide variation in the reaction temperature is possible, but it generally ranges from 60° to 100° C.

Once the reaction is complete, it is possible to lower the pH of the reaction medium, e.g., to a value of approximately 4. It is also possible to conduct an aging steep over a period of from, e.g., 30 minutes to 1 hour. The lowering of the pH upon completion of the reaction makes it possible to convert the remaining silicate into silica and thus obtain a particle surface which is not excessively basic.

The second variant comprises preparing the silica from a sediment incorporating a silicate solution. In other words, an aqueous silicate solution is first formed and the dye is introduced therein. The dye is maintained in the dispersed state in the solution by appropriate agitation, followed by the addition of an acid.

In this second variant, the temperature conditions are identical to those of the first variant. Obviously, an aging step can also be effected.

The separation of the pigment formed from the liquid phase of the reaction medium obtained according to the described processes then takes place in per se known manner. The separated pigment is then dried.

As regards the silicate, alkaline silicates are generally used, and more especially sodium, potassium or lithium silicates. In known manner, silicates are used in a molar ratio generally ranging from 2 to 4.

The acid is typically sulfuric, nitric, hydrochloric or a carboxylic acid.

A second process will now be described, which essentially consists of preparing the silica by the hydrolysis of an alkyl silicate. More specifically, a dye and an alkyl silicate are admixed, the alkyl silicate is hydrolyzed and the resulting pigment and the liquid phase are separated from the reaction medium.

This is in fact the most commonly used technique, as described in the article by Stöber et al, *Journal of Colloid and Interface Science*, 26, pp. 62-69 (1968), hereby expressly incorporated by reference.

It is generally preferable to carry out the hydrolysis in the presence of a base, which serves as the catalyst.

A reaction medium is formed by mixing water, alcohol and optionally a base, and then introducing the alkyl silicate, the dye or dyes either being introduced simultaneously, or are already present in the reaction medium prior to the introduction of the alkyl silicate.

Ammonia can be used as the base. The alcohols used are typically aliphatic alcohols. The reaction typically takes place at ambient temperature and the alkyl silicate is preferably introduced with an alcohol.

It is also possible to form a sediment based on alcohol, dye and alkyl silicate and then introducing water or a water-base mixture therein. The alkyl silicate is advantageously ethyl silicate.

As described hereinbefore, the resulting pigment is separated from the reaction medium, typically washed with alcohol, and then dried.

Several different techniques can be used in the preparation of alumina-based colored pigments According to a first technique, the reaction medium is formed by intimately contacting at least one dye, an aluminate and an acid. Several variants are possible. Thus, it is possible to simultaneously introduce the aluminate and the acid, the dye being present as sediment prior to the simultaneous introduction, or in another case the dye is introduced simultaneously. The procedure can be such that the pH of the reaction medium is maintained constant In another variant, it is possible to begin with an aluminate solution, into which is introduced the dye and simultaneously or subsequently the acid. In general, an alkaline aluminate is used. The acid used can, e.g., be hydrochloric or nitric acid.

In a second preparative technique, the alumina-based pigment is prepared by forming a reaction medium by intimately contacting at least one dye, an aluminum salt and a base.

Obviously, the variants described for the earlier method are also applicable here. Thus, it is possible to begin with a sediment constituted by a solution of the aluminum salt, prior to the simultaneous or separate introduction of the dye and the base. The base is typically soda or ammonia, while the aluminum salt can, e.g., be an aluminum halide, such as aluminum chloride or aluminum nitrate.

This variant is similar to that described hereinbefore, for the hydrolysis of an alkyl silicate.

The procedure continues by intimately contacting at least one dye and an aluminum alkoxide, followed by the hydrolysis of the latter and the separation of the resulting pigment and the liquid phase from the reaction medium.

The earlier description in the case of the hydrolysis of an alkyl silicate applies here with respect to the use of a base, and the manner in which the reagents are introduced.

The alkoxide can be aluminum methylate, ethylate, isopropylate or butylate, said alkoxides being in liquid or solid form in dispersion or in solution in an organic solvent, e.g., benzene or the corresponding alcohol.

In the case of the preparation of titanium dioxide-based colored pigments, the titanium dioxide can be prepared in the presence of the dye or dyes according to different methods.

The first comprises intimately contacting the support, at least one dye and a titanium (IV) salt, hydrolyzing the latter and separating the thus formed pigment and the liquid phase from the reaction medium. More specifically, said hydrolysis can take place on the basis of titanium (IV) sulfate sulfuric solutions. After evaporation with a view to providing a concentrated solution, these solutions are mixed with hot water at a temperature of approximately 95° C., the mixture being maintained boiling. Thus, a precipitate is collected.

In such a case, the dye is present from the outset in the titanium (IV) sulfate solution.

Another embodiment includes effecting a hydrolysis of the $TiCl_4$ chloride, with the addition of ammonia. The dye can be present in the $TiCl_4$ starting solution.

A third embodiment includes hydrolyzing an alkyl titanate. The latter is identical to the methods described hereinbefore in connection with the hydrolysis of an alkyl silicate or an aluminum alkoxide. The earlier description in connection with the method of introducing the reagents also applies here.

As regards the preparation of colored pigments incorporating zirconium oxide as the mineral oxide, such preparations are of the same type as described above for titanium dioxide.

The pigments according to the invention have numerous applications in all fields entailing the use of colored charges. Thus, they can, e.g., be used in the preparation of cosmetics, detergent compositions and glues.

Apart from their good chemical resistance, the pigments according to the invention have a very considerable dispersibility.

Thus, they can be used in the preparation of dentifrice compositions. Indeed, it is difficult to disperse in toothpastes the dyes which are usually added to these compositions and it is then necessary to add surfactants. Moreover, the coloration is not lasting and deteriorates over the course of time.

In the case of the pigments of the invention, introduction thereof into toothpastes is readily accomplished by reason of the good dispersibility thereof.

Moreover, it is observed that there is no change of color over the course of time. The dyes used in this respect are, for example, those dyes such as chlorophyllin, thymol blue, and green pigment (C.I. 74260), fluorescein (C.I. 4350), white pigment (C.I. 74160).

These pigments can also be advantageously used in the production of developing powders of the electrostatic type, for electrographic or xerographic processes.

This use of the pigments according to the invention entails no modifications with respect to the formulation of the aforementioned powders. Thus, apart from the pigment, they could contain all conventional ingredients, such as binders and other additives, such as, e.g., filler materials.

In order to further illustrate the present invention and the advantages thereof, the following specific examples are given, it being understood that same are intended only as illustrative and in nowise limitative.

EXAMPLE 1

Preparation of Colored Spherical Silica Particulates:

Into a 4 liter stainless steel reactor equipped with a Mixel-type agitator or stirrer and counter-blades, the following reagents, constituting the sediment, were introduced:
96° alcohol 2,000 ml
NH$_4$OH (240 g/l) 398 ml
Soft water 114 ml
Bayer Bayplast red dye 1 g At ambient temperature, a mixture of 775 ml of ethyl silicate Si(OEH$_2$)$_4$ and 213 ml of ethanol was introduced at a rate of 25 cm$^3$/min. The colored suspension was then filtered on a Büchner filter, the filtrate was washed with alcohol at 90° C., dried in air for 15 minutes and then at 120° C. for 4 hours. The mean diameter of the silica particles: 0.75 μm.

EXAMPLE 2

Preparation of Colored Silica Particulates

Into a 3 liter stainless steel reactor equipped with a turbine-type agitator having four blades, each 45 mm in diameter, a mixture of 500 cm$^3$ sodium silicate with a Rm molar ratio SiO$_2$/Na$_2$O of 3.4, 380 g/l of SiO$_2$ and 1,000 cm$^3$ of soft water was first introduced. The solution, stirred or agitated at 400 r.p.m., was heated to 80° C. and maintained at this temperature by regulation. This was followed by the progressive dispersion therein of 2 g of Ciba Geigy 133 R Irgalithe yellow dye. Using a dosing pump and a flow rate of 45.6 cm$^3$/min, 930 cm$^3$ of 9% H$_2$SO$_4$ were added over 20 minutes. The pH, which was 10.6 at the beginning of the operation, decreased to 8.6 upon completion of this introduction. By a supplementary addition of 250 cm$^3$ of 9% H$_2$SO$_4$, the pH was adjusted to 7.5. The mixture was filtered on a Büchner filter and filtered on paper, followed by washing with 3 times its volume of soft water. The product was dried in an oven at 120° C. for 15 hours.

EXAMPLE 3

Preparation of Colored Titanium Oxide Particulates

The starting material was a sediment consisting of 250 ml of butanol and a Ciba Geigy Irgalithe red dye. At 60° C. and under stirring using a turbine mixer at 200 r.p.m., 1 liter of Ti(OBu)$_4$ to 68 g/l in 1-butanol and 1 liter of H$_2$O to 14.4 g/l in 1-butanol were simultaneously added over 1 hour, followed by filtration, washing and drying.

EXAMPLE 4

Preparation of Colored Alumina Particulates

Into a 3 liter reactor, under stirring using a turbine mixer at 800 r.p.m., 2 liters of an aqueous solution containing 5.5 g of Na$_2$SO$_4$ and 0.1 g of Ciba Geigy Irgalithe red dye were introduced.

This was followed by addition of 15 cm$^3$ of 2-butanol containing 5 g of aluminum butylate (Al(OBu)$_3$) over 30 min. The mixture was then heated to 95° C. over 2 hours and was then permitted to age for 20 hours. The mixture was then filtered on a 0.8 μm Millipore filter and washed with soft water. The product was dried in an oven at 130° C. for 15 hours. After grinding, it had a red color.

EXAMPLE 5

Preparation of Colored Alumina Particulates

Into a 1 liter reactor, under stirring using a 4 blade turbine mixer at 800 r.p.m., 200 cm$^3$ of soft water and 1 g of mordant blue 3 (Color Index 43 820) were introduced. The mixture was heated to 70° C.

This was followed by the simultaneous addition of a sodium aluminate solution (100 g of Al$_2$O$_3$ in 300 cm$^3$ of H$_2$O) at a constant flow rate of 10 cm$^3$/min, and 5% H$_2$SO$_4$. The H$_2$SO$_4$ flow rate was adjusted to maintain the pH at a constant value of 8.

The mixture was then permitted to age for 1 hour and then the pH was decreased using 5% H$_2$SO$_4$. The mixture was then filtered on the Büchner filter. The washing was with soft water. The product was dried in an oven at 130° C. for 15 hours. After grinding, it had a blue color.

EXAMPLE 6

This example illustrates the behavior with respect to coloration by solvents of the colored pigments according to the invention.

A hermetically plugged 50 cm$^3$ tube was used, into which were introduced 1 g of the pigment to be tested of Examples 2 and 5 and 20 g of solvent, which was water, methanol (MeOH) or heptane ($C_7$). The medium was homogenized by placing the tube into a TURBULA agitator for 2 hours. This was followed by observation of the sedimentation for 1 hour, 24 hours and 48 hours.

The results are reported in the following Table. It will be seen that the dyes of the pigments according to the invention were not eliminated by washing with water, methanol and heptane. The cloudy coloring of Example 2 was due to the slow sedimentation of the pigment in the solvent.

TABLE

| Pigment | Solvent | Time in Hours | | |
|---|---|---|---|---|
| | | 1 | 24 | 48 |
| Example 2 | $H_2O$ | Colorless | Colored | |
| | MeOH | Colored Cloudy | Colored Cloudy | Colorless |
| | $C_7$ | Colorless | | |
| Example 5 | $H_2O$ | Colorless | | |
| | MeOH | Colorless | | |
| | $C_7$ | Colorless | | |

EXAMPLE 7

Preparation of Colored Silica Particulates for Dentifrice

Into a reactor, 6 liters of deionized water were introduced and, under stirring, 10.2 g of chlorophyllin in hydrosoluble powder form were added thereto. Heating, under stirring, was continued up to 85° C. When this temperature was reached, 8.5 liters of sodium silicate (d=1.112), at a flow rate of 0.340 1/min, and 1.35 liters of sulfuric acid (80.0 g/l) at a flow rate of 0.210 1/min, were simultaneously introduced into the reactor.

The sulfuric acid flow rate was adjusted such as to maintain the pH of the medium at a constant value of 8. Simultaneous addition occurred over 40 minutes The mean pH during the reaction was 8.0.

Upon completion of the simultaneous addition, the reaction mixture was permitted to age for 10 minutes at pH 8. The pH was then stabilized at 5 by sulfuric acid addition. 15 minutes of aging were carried out at a pH of 5 and at 85° C.

The mixture was then filtered and the resulting filter cake was washed with deionized water. The silica was dried in an oven at 120° C. for 6 hours. The silica obtained was then ground to produce a mean particle diameter of 3 microns. The resultant silica was characterized by a BET surface of 70 $m^2/g$ and a green color, enabling the production of green toothpastes.

EXAMPLE 8

Into a reactor equipped with temperature and pH regulation and fitted with a turbine-type agitator, 6 l of deionized water and 100 g of blue dye (C.I. 74180) were introduced.

After the agitator was started (300 r.p.m.), the solution was heated to 85° C.

When this temperature was attained, 8.5 l of sodium silicate of a silica concentration of 120 g/l, having a ratio $SiO_2/Na_2O$ of 3.5, at a flow rate 0.34 1/min, and 13.5 of sulfuric acid having a concentration of 80 g/l were simultaneously added thereto. The acid flow rate was adjusted such as to maintain the pH of the medium at a constant value of 8.0.

After 40 min of addition, the silicate addition was terminated but the acid addition was continued to stabilize the pH of the reaction medium at 4. 15 minutes of aging was carried out at this pH and at 85° C. The mixture was then filtered and the wet filter cake was washed with deionized water.

The product was flash dried and ground in a forplex type grinder to provide a granulometry of 10 microns. The silica had a BET surface of 60 $m^2/g$ and a blue color. The following dentifrice composition was used (percentages are by weight):

Glycerine 22%
Carboxy methylcellulose 1%
Blue colored silica 31%
Sodium benzoate 0.1%
Sodium saccharinate 0.2%
Sodium fluoride 0.1%
Flavoring 0.9%
Water 37%

The toothpaste obtained was easily extruded and had good brush-holding qualities.

The use of the colored silica made the formulation easier.

The dispersibility thereof was perfect, very rapid and the preliminary addition of surfactants was not necessary.

Moreover, no adverse aging effects were noted after 6 months at 120° C.

EXAMPLE 9

This example illustrates the preparation of a silica for developing powders.

Into a 3 l reactor equipped with turbine type agitator, temperature and pH regulator, 1,000 ml of water and 500 ml of sodium silicate of a silica concentration of 380 g/l, and of Rm=3.5, were introduced.

At 80° C. and under stirring, 2 g of CIBA Irgolithe 2GP dye were dispersed. Then, 900 ml of $H_2SO_4$ (10%) were added over 40 minutes. After 15 minutes of aging, the pH was decreased to 5 by addition of $H_2SO_4$ (10%). The mixture was filtered and washed, then dried at 120° C. for 4 hours. The resulting pigment was ground using a Jet Pulverizer type micronizer.

EXAMPLE 10

The above procedure was repeated, to produce pigments of different colors, using the following dyes:

| Yellow | Microlithe 2GT | (CIBA) |
|---|---|---|
| | Irgalithe 2GB | (CIBA) |
| Magenta | Rubine Irgalithe CPBC | (CIBA) |
| | Rubis lithiol | (BASF) |
| | Isol 4BK | (KVK) |
| Cyan | Blue heliogene D 7072 | (BASF) |
| | Isol G4B | (KVK) |

EXAMPLE 11

The transparency of the pigments being a prerequisite for the use thereof in the production of developing powders, this example illustrates the tests for measuring the light transmitted by a film.

1 part by weight of pigment was dispersed into a solution consisting of 10 parts by weight of polyester resin (NORSODYNE type of CDF) and 100 parts of tetrahydrofuran.

The dispersion was deposited as a 3 μm thick layer on an polyester film having a thickness of 50 μm.

The density of transmitted light (inverse of transmittance logarithm) was measured by means of a densitometer.

The transmitted light density of two coatings prepared according to the above method were compared, as ported hereinbelow.

Coating A was produced using pure pigment (Irgalithe 2GP) and coating B was produced using the silica pigment of Example 9.

| Thickness of the layer μm | Transmitted light density | |
|---|---|---|
| | Pigment A | Pigment B |
| 3 | 0.6 | 0.1 |

The colored silica pigments were the more transparent.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A pigmentary colorant material consisting essentially of a particulate mineral oxide selected from the group consisting of silica, titanium oxide, alumina and zirconium, oxide and at least one dye, said at least one dye being wholly incorporated and physically confined within a matrix of the particulate mineral oxide said dye being present in an amount sufficient to totally mask the color of the mineral oxide.

2. The pigmentary colorant material as defined by claim 1, said mineral oxide comprising a hydrated oxide, of silica, aluminum, titanium or zirconium.

3. The pigmentary colorant material as defined by claim 1, said at least one dye comprising from 0.001 to 10% by weight of the mineral oxide.

4. The pigmentary colorant material as defined by claim 1, said at least one dye comprising a cationic or basic dye and the mineral oxide comprising silica.

5. The pigmentary colorant material as defined by claim 1, said at least one dye comprising an anionic or acidic dye and the mineral oxide comprising alumina.

6. The pigmentary colorant material as defined by claim 1, said at least one dye comprising a hydrosoluble dye.

7. The pigmentary colorant material as defined by claim 1, said at least one dye comprising an alcohol-soluble dye.

8. A process for the preparation of pigmentary colorant material consisting essentially of at least one dye and a particulate mineral oxide selected from the group consisting of silica, alumina, zirconium oxide and titanium oxide, comprising intimately contacting a precursor of said particulate mineral oxide and the at least one dye, next coprecipitating or crystallizing the oxide/dye under conditions effective to confine said at least one dye throughout a matrix of the particulate oxide, and then recovering the pigmentary colorant material.

9. The process as defined by claim 8, said intimately contacting step being carried out in the presence of the at least one dye, a silicate comprising the precursor of said mineral oxide and an acid.

10. The process as defined by claim 8, said intimately contacting step being carried out in the presence of the at least one dye, an aluminate comprising the precursor of said mineral oxide and an acid.

11. The process as defined by claim 8, said intimately contacting step being carried out in the presence of the at least one dye, an aluminum salt comprising the precursor of said mineral oxide and a base.

12. The process as defined by any of claims 9, 10 or 11, said intimately contacting step being carried out by simultaneously introducing the acid or base, together with said silicate, aluminate or aluminum salt.

13. The process as defined by claim 8, wherein the pH during the intimately contacting step is maintained constant.

14. The process as defined by claim 8, comprising aging said pigmentary colorant material upon preparation thereof.

15. The process as defined by claim 9, comprising hydrolysis of an alkyl silicate.

16. The process as defined by claim 11, comprising hydrolysis of an aluminum alkoxide.

17. The process as defined by claim 8, comprising hydrolysis of a titanium (IV) salt.

18. The process as defined by claim 8, comprising hydrolysis of an alkyl titanate.

19. The process as defined by claim 8, further comprising washing and drying said pigmentary colorant material recovered.

20. A dentifrice composition comprising the pigmentary colorant material as defined by claim 1.

21. An electrostatic developer powder comprising the pigmentary colorant material as defined by claim 1.

22. The pigmentary colorant material as defined by claim 1, further comprising a binder or filler material.

23. The process as defined in claim 8, wherein said dye is maintained in a dispersed state in a solution during said intimately contacting step.

24. A pigmentary colorant material consisting essentially of a particulate mineral oxide selected from the group consisting of silica, alumina, zirconium oxide and titanium oxide and at least one dye, said at least one dye being wholly incorporated and physically confined within the matrix of the particulate mineral oxide said dye being present in an amount sufficient to totally mask the color of the mineral oxide and protected by an oxide layer of the particulate mineral oxide.

* * * * *